(12) United States Patent
Lipman (10) Patent No.: US 6,659,964 B2
(45) Date of Patent: Dec. 9, 2003

(54) SONAR-CONTROLLED APPARATUS FOR THE DELIVERY OF ELECTROMAGNETIC RADIATION

(75) Inventor: Jonathon Lipman, Libertyville, IL (US)

(73) Assignee: Neuroscience Tool Works, Inc., Evanston, IL (US)

(*) Notice: Subject to any disclaimer, the term of this patent is extended or adjusted under 35 U.S.C. 154(b) by 0 days.

(21) Appl. No.: 10/109,306

(22) Filed: Mar. 28, 2002

(65) Prior Publication Data
US 2002/0188218 A1 Dec. 12, 2002

Related U.S. Application Data

(63) Continuation of application No. PCT/US00/41672, filed on Oct. 26, 2000.
(60) Provisional application No. 60/162,441, filed on Oct. 27, 1999.

(51) Int. Cl.[7] .............................. A61B 19/00; A61B 5/00
(52) U.S. Cl. ........................ 600/557; 600/549; 600/555
(58) Field of Search ........................ 600/549, 555–557, 600/407, 473; 606/2, 8–13; 607/88, 89, 96–100; 219/121.61, 121.62; 250/205, 559.29, 559.38; 356/3, 3.07, 3.14, 486; 367/88, 99

(56) References Cited

U.S. PATENT DOCUMENTS 4,622,971 A 11/1986 Yamamoto et al.
5,015,868 A 5/1991 Park
5,354,323 A 10/1994 Whitebook
5,941,833 A 8/1999 Lipman
6,248,079 B1 * 6/2001 Lipman ..................... 600/555

FOREIGN PATENT DOCUMENTS

DE 195 38 382 4/1996
DE 196 47 676 5/1998
WO WO 97 12559 4/1997

OTHER PUBLICATIONS

International Preliminary Examination Report, for International application No. PCT/US00/41675, mailed on Dec. 19, 2002 (7 pages).
International Search Report for International Application No. PCT/US00/41672, mailed Apr. 3, 2001.

* cited by examiner

Primary Examiner—Charles A. Marmor, II
(74) Attorney, Agent, or Firm—Fitch, Even, Tabin & Flannery

(57) ABSTRACT

The present invention comprises devices and methods that deliver electromagnetic radiation (EMR) from an emitter to a target and employ a laser or sonar (a sensing method) to measure distance between the target and EMR emitter and automatically signal the emitter control circuitry to vary either the position or the power output of the emitter (as appropriate) in order to ensure that the effect of any change in distance on the energy incident to the target is compensated rapidly and automatically. In a preferred embodiment, the device is a hand-held, non-contact heatbeam dolorimeter.

5 Claims, 7 Drawing Sheets

COMPARISON OF TIME VS. TEMPERATURE PROFILES OF PHASE 0 HBD AND PHASE 2B DEVICE UNDER STATIC CONDITIONS, AND FOR THE PHASE 2B DEVICE, AT DIFFERENT DISTANCES

SONAR-CONTROLLED APPARATUS FOR THE DELIVERY OF ELECTROMAGNETIC RADIATION

This application is a continuation of PCT/US00/41672 filed Oct. 26, 2000, and claims the benefit of provisional application No. 60/162,441 filed on Oct. 27, 1999.

The invention described herein was funded, in part, by grant number R43 NS 34616 from the National Institutes of Health, and is subject to a nonexclusive licensing agreement with the United States government.

BACKGROUND OF THE INVENTION

The invention relates to devices that use sonar to automatically control the delivery of electromagnetic radiation, including heat and light, to a target. In a preferred embodiment, the invention relates to sonar control of the delivery of radiant heat to the skin for the measurement of pain tolerance limits.

In applications where electromagnetic radiation (EMR) projected from an emitter is directed at a target, under conditions where distance may undesirably change between emitter and target, there is a need for automatic control processes that regulate the delivery rate of the EMR received at the target by adjusting the output of the emitter mechanism, the projector of heat or light or other EMR.

A true feedback mechanism would use a sensor, positioned at or within the target, to feedback-control either the power output or position—the emitter-target distance—of the emitter, thus ensuring that these characteristics of the emitter are rapidly and automatically adjusted to maintain target (and sensor) irradiation within set limits.

Unfortunately, available sensor response characteristics are largely inadequate to this task. Thus, should a temperature sensor within the target be used to feedback control a motor-drive positioning mechanism (for instance) on which a radiant heat projector (emitter) is mounted, and the feedback from the sensor be used to control projector position, either toward or away from the target, it is found that accurate, rapid and responsive positioning of the emitter by the motor drive cannot be achieved because the sensor response time is invariably too slow, having too much inertia or resistance to change. The same is true of light and other forms of EMR.

When the emitter is employed as a sensory stimulator for testing human cutaneous sensibility, it is essential that the energy delivered to the skin be precisely controlled. Since delivered energy is a proportional function of the power of the emitter and the distance of the emitter to the skin target, both must be held constant to achieve adequate stimulus control. An earlier form of the computerized Heatbeam Dolorimeter (HBD) achieved this control by means of a precisely regulated power supply to the emitter, an infra-red (or heat or light) emitter, coupled with an articulated arm which allowed accurate positioning and an arrangement of intersecting visible lasers for guiding the precise positioning of the device at the correct emitter-target distance (Lipman J., U.S. Pat. No. 5,941,833).

Cutaneous sensory testing devices are employed in evaluating the state and the health of both the peripheral nervous system and the central nervous system and the central pain perceptual processes of the brain. Such testing devices employ some type of stimulus, either mechanical (tactile, pressure, vibration) thermal, electrical or of other modality, and assess the subject's ability to detect and respond to the stimulus. Of particular relevance to the present invention is the sensory examination of the human pain continuum by means of sensory testing devices. The cutaneous range of pain sensation of the skin, called the 'pain sensibility range' which is modality-specific, is bounded at the lower end of the stimulus intensity spectrum by the pain threshold, defined in terms of the stimulus intensity that is perceived as just noticeably painful by the subject. At the upper end of the pain sensibility range lies the pain tolerance limit, defined as the maximum possible pain stimulus intensity that the subject can tolerate. The pain tolerance limit has also been called the 'reaction limit' or 'reaction threshold' by some authors (Hardy J D, Wolff H G, Goodell H (1952). *Pain Sensations and Reactions*, Williams and Wilkins Co, Baltimore, 1952), because it is accompanied by reflexive aversive withdrawal of the subject from the stimulus.

Tactile methods, such as that described in Horch et al. (U.S. Pat. No. 5,022,407 Apparatus for Automated Tactile Testing), apply stimulator elements or electrodes held in close physical contact with the skin, which transmit vibration or pressure or pin prick stimuli. Thermal methods, of which a preferred embodiment of the present invention is a particular variation, transmit heat to the skin either through a peltier-type heating electrode in contact with the skin (see: Lautenbacher S & Rollman G B (1991) *Sex differences in responsiveness to painful and non-painful stimuli are dependent upon the stimulation method*. Pain 53:255–264) or by radiant heat means using infra-red (see: Hardy J D, Wolff H G, Goodell H (1952), *Pain Sensations and Reactions*, Williams and Wilkins Co, Baltimore, 1952; and see: Lipman J J, Blumenkopf B & Parris W C V (1987) *Chronic pain assessment using heatbeam dolorimetry*. Pain 30:59–67) or laser irradiation (Svensson et al., (1991) "*Comparison of four laser types for experimental pain stimulation on oral mucosa and hairy skin,*" Lasers in Surgery and Medicine 11:313–324). Radiant heal methods of generating the stimulus to be used in pain threshold measurement may themselves be of either contact or non-contact application. Thus, one skin-contacting method proposed as suitable for forearm testing uses a horizontal glass plate on which the user rests their arm and through which a radiant beam of heat is directed (see Hargreaves et al., U.S. Pat. No. 5,025,796, Apparatus and Methods for determining in vivo response to thermal stimulation in an unrestrained subject). Likewise, a non-contact method (Hardy et al, ibid) has been used in pain threshold measurement at various body sites.

For measurement of the thresholds of cutaneous sensory pain-evoking modalities, of pressure, of mechanoceptive tactile sensibility, of heat pain and of electrical pain, the skin-contacting types of devices (here called "contact devices") are both convenient to use and adequate in interpretation. In measurement of pain tolerance limits, however, devices which stimulate more than one modality (touch and heat, for instance) interfere with the sensory perception of each discrete sensory mode. Thus, pain tolerance to a heat (thermal) stimulus is altered by mechanoceptor (touch) stimulation. In measuring thermal pain tolerance, a skin-contacting method of heat delivery cannot be used, therefore and a pure unimodal non-contact stimulus is absolutely necessary. Prior inventions have addressed the problem of pressure (touch stimulation) interference on thermal pain sensibility by attempting to control and standardize the degree of pressure applied by the heat-delivering element (see Guillemin, U.S. Pat. No. 2,728,337) but the ideal solution to the problem of sensory interference is to be found in completely obviating the confounding non-thermal stimulus entirely.

The HBD device and method was developed to take advantage of this non-contact sensory requirement of pain tolerance measurement—the device stimulating the subject's skin by means of radiant heat and light without interfering mechanoceptor (touch sensation) stimulation. An earlier version has been described in which a radiant beam of heat and light, carefully calibrated and of constant power output and hence stimulus energy characteristics, employs two focused visible lasers to position the device at the correct distance from the skin, yet which may be carefully hand-held, and which employs a remote-sensing thermocouple to measure skin temperature during stimulus application (Lipman, U.S. Pat. No. 5,941,833 Heatbeam Dolorimeter for Pain and Sensory Evaluation). This Basic HBD device is mounted on a spring-loaded articulated support arm and is manually positioned by the operator at the appropriate distance from the various test sites around the body of the subject.

There remains a need however, fulfilled by the present invention, for an improved hand-held form of the above-described "basic Heatbeam Dolorimeter" device that can be conveniently employed in situations where examination room space is limited and an articulated positioning arm inconvenient. The ideal improvement would render the HBD capable of automatically maintaining the proper skin-heating stimulus characteristics even under conditions where the operator's hand may tremble or move or may spatially drift toward or away from the skin during the application of the stimulus. Because of the inverse square law, which applies to radiant EMR including that which generates heat, such inadvertent movement of a constant-power heat radiator would greatly increase skin heating rate as the device moved toward the skin and greatly decrease such rate as the device moved away. Movement in either direction would invalidate the measurement of pain tolerance limit.

The present invention overcomes these deficiencies in the prior art. The invention capitalizes on the constant and reliable relationship of distance and intensity that characterizes EMR propagation over distance and the speed and accuracy of distance measurement using sonar at short ranges. Therefore, the present invention provides a device and method which delivers EMR, such as heat, in an automatically controlled feedback manner, based on distance measurements of a sonar sensor. Additionally, the present invention fulfils a need for an improved hand-held form of the device, which is convenient to maintain at an appropriate and constant distance without the assistance of an articulated arm.

DESCRIPTION OF THE RELATED ART

Lipman, U.S. Pat. No. 5,941,833 entitled: "Heatbeam Dolorimeter for Pain and Sensory Evaluation" describes a heat beam dolorimeter for measuring pain tolerance. The dolorimeter is mounted on a spring-loaded articulated support arm and is manually positioned by the operator at the appropriate distance from the various test sites around the body.

Hargreaves et al, U.S. Pat. No. 5,025,796 entitled "Apparatus and Methods for determining in vivo response to thermal stimulation in an unrestrained subject" describes a radiant heat pain stimulator that for adjustment of emitter-target distance relies on contact with the skin of the target site either by a wire cage or by a glass sheet on which the test animal or person rests.

Guillemin, U.S. Pat. No. 2,782,337 entitled "Diagnostic Apparatus" describes a contact-type heat stimulator which attempts to control the interfering effect of variation in pressure by regulating the degree of pressure applied.

Belanger, et al. U.S. Pat. No. 4,817,301 entitled "Apparatus for drying vehicles" describes a sonar-directed control means for positioning an air dryer nozzle in relation to a vehicle being dried.

Wentworth, U.S. Pat. No. 5,722,104 entitled "Position control system for counterweighted vehicle laundry top brush" describes the use of a sonar method to control the position of a brush used to wash vehicles.

Springer, U.S. Pat. No. 5,765,995 entitled "Automated engine-powered pump control system" describes the application of a sonar sensing system in detecting water level drained by a pump.

Massa, U.S. Pat. No. 4,103,309 entitled 'Automatic camera focusing means' describes a method of automatically controlling a movie camera focusing device by a sonar device measuring distance to the object photographed.

SUMMARY OF THE INVENTION

The present invention provides a device and method which delivers EMR, such as heat, in an automatically controlled feedback manner, based on distance measurements of a distance sensor. In a preferred embodiment, the device is a sonar-regulated Heat Beam Dolorimeter (HBD), a human cutaneous sensory testing device, capable of hand-held operation in a non-contact manner in the elicitation and measurement of the pain tolerance limit.

A first general embodiment of the invention provides a non-contact apparatus for regulating the delivery of electromagnetic radiation to a target site, said apparatus comprising:

a non-contact emitter;

a distance sensor; and an emitter control device, wherein said delivery of electromagnetic radiation is automatically regulated as a function of target-site distance through interaction of the distance sensor and the emitter control device.

In a preferred embodiment of the first general embodiment of the invention, the distance sensor is a sonar ranging sensor. In another preferred embodiment, the automatic regulation of the projection of electro-magnetic radiation provides a controlled effect at the target site when target-site distance changes within an effective control range. In another preferred embodiment, the electro-magnetic radiation comprises infrared radiation and the distance sensor is a non-infrared laser.

In another preferred embodiment of the first general embodiment the non-contact emitter is a radiant heat source, the distance sensor is a sonar-ranging sensor, and the emitter control device is a radiant heat source control device. In this embodiment, preferably said apparatus provides an automatically controlled heating rate at the target site when the target-site distance changes but remains within an effective distance range. In this embodiment, preferably the target site is a site on a subject's skin and the apparatus is a dolorimeter for determining pain tolerance, said apparatus further comprising a non-contact temperature-measuring device, wherein said apparatus is capable of being employed for determining pain tolerance without tactile stimulation of the site on the subject's skin by said apparatus or by any other means. Preferably, the apparatus further comprises a hand-held fixture, wherein the dolorimeter is capable of being held by a dolorimeter operator.

In a second general embodiment, the invention is a method for regulating the delivery of heat to a target site comprising the steps of:

(a) delivering electro-magnetic radiation;
(b) determining a target-site distance during the step of delivering electro-magnetic radiation; and
(c) automatically regulating the delivery of electromagnetic radiation as a function of the target-site distance.

In this method, preferably the step of determining the target-site distance utilizes sonar and the step of automatically regulating the projection of heat provides a controlled effect at the target site when the target-site distance changes but remains within an effective distance range. In another preferred embodiment the step of delivering electro-magnetic radiation comprises delivering infrared radiation and the step of determining the target-site distance utilizes a non-infrared laser beam.

In another preferred embodiment the step of delivering electro-magnetic radiation comprises delivering radiant heat and the step of determining the target-site distance utilizes sonar. Preferably, said step of automatically regulating provides a controlled effect at the target site when the target-site distance changes within an effective control range. In a further preferred embodiment the target site is a site on a subject's skin, said method further comprising determining temperature of the target site without contacting the target site, wherein said method is capable of determining pain tolerance without tactile stimulation of the site on the subject's skin. In a further preferred embodiment, the method further comprises providing an apparatus for carrying out the steps of delivering radiant heat, determining the target-site distance, automatically regulating the projection of heat, and determining the temperature of the target site. Preferably the apparatus allows the method to be carried out while the dolorimeter is held by a dolorimeter operator.

In another preferred embodiment of the first general embodiment the non-contact emitter is a light source, the distance sensor is a sonar ranging sensor, and the emitter control device is a light source control device. Where the non-contact emitter is a light source, preferably the apparatus provides a controlled amount of energy at the target site when the distance of the light source to the target site changes but remains within an effective distance range.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE PREFERRED EMBODIMENTS

Definitions: In this specification and appended claims, unless specified to the contrary, the term:

"Apparatus for regulating delivery of Electro-Magnetic Radiation (EMR)" refers to an apparatus that generates, propagates and directs a beam of EMR at a target and regulates the intensity of radiation incident upon the target, including regulation in response to movement of the target. Preferably, incident radiation intensity is maintained substantially constant at the target, most preferably constant, regardless of distance within an effective control range. Examples of these apparatuses include, but are not limited to, radiant heat projecting devices including heatbeam dolorimeters, warming lamps, for example warming lamps used in pediatric care, paint-drying and enamel-baking heat radiators, radiators for target incineration, and for surface etching and the like; ultraviolet projecting devices for curing plastics, for setting EPROM devices, for tanning purposes, for use in psoralen or other photoreactive therapies, for fingerprint visualization and the like; X-ray devices for medical imaging, metal fracture examination and similar applications, laser projectors for cutting, etching and curing purposes, visible light devices for film processing, for photoreactive chemistry and for optical and optoelectronic signaling purposes, where incident radiation intensity delivered to the target must be automatically regulated as the emitter target distance may chance.

"Pain tolerance limit" refers to the upper boundary of the pain sensibility range, the lower boundary of which is known as the 'pain threshold.'

"Support" refers to the mechanical frame or assembly, hand-held or otherwise, to which are mounted the sensor and emitter elements of the device. In the simplest arrangement both share the same support, but other configurations are possible.

"Non contact emitter" refers to the emitter or source of EMR, which does not physically touch the target being irradiated. It may be a radiant projector of heat or light or EMR of any wavelength. Typically, it is a visible light photographic film-type projector lamp, an infra-red emitter, or an ultraviolet projector or, in certain applications, an X-ray lamp.

"Light Source" refers to the non-contact emitter when this is employed in an application to deliver light.

"Controlled effect" refers to the regulation, preferably precise regulation, of incident radiation at the target according to a desired profile of energy delivery, which may be substantially constant, constant or variable as required by the specific application.

"Controlled energy rate" refers to the controlled effect where this is employed in an application that delivers EMR which may be other than heat-generating energy.

"Controlled heating rate" refers to the controlled effect of EMR where this is employed in an application that delivers heat. For the HBD in normal use this is 1.93 Deg C./Sec and may be adjusted to other values.

"Automatic regulation" refers to the completely autonomous regulation by circuitry and a computer program of the emitter control means in response to signals received from the distance sensor.

"Electro-Magnetic Radiation" refers to the radiated energy field emitted by the passage of electrons through a material conductor, such as a lamp filament, and may span the EMR spectrum from gamma rays, X-rays, visible light, infra red through ultra-violet and microwave radiation.

"Non-contact temperature measuring device" refers to a thermocouple thermopile, infra-red or other direct or indirect thermal radiation sensing device capable of measuring the temperature of a target without making physical contact with the target, for example, by quantifying infra-red radiation emitted by that target.

"Effective control range" refers to the distance over which target irradiation can be effectively controlled within desired parameters by accurately yoking the emitter control to the distance sensor response, and is a function of the limitations of both distance sensor and the emitter. For example, for the sonar-controlled heatbeam dolorimeter this may be a range of less than six inches, in one embodiment two inches (one inch further than and one inch nearer than the optimal target distance). For other applications and emitter—sensor pairs this could be very much greater (for paint drying purposes, for tanning or for incineration) or very much shorter (for UV curing of dental resins, plastics and like applications).

"Emitter control device" refers to the means of powering the emitter at a particular and desired intensity, including— in the case of the present invention—a means of overcoming and neutralizing changes in distance between emitter and target. This may be achieved, for example, by a variable positioning mechanism such as a motor drive or a variable and regulated power supply of a stationary emitter, or both. Preferably the emitter control device is capable of rapidly changing (ie. one hundred milliseconds or faster) the emission intensity incident at the target from one value to another different value in response to a control signal provided by the control circuits and computer software in response to signals from the distance sensor.

"Distance sensor" refers to a device for measuring the spatial separation of target and emitter, in certain preferred embodiments, without physically touching the target. It may employ sonar, laser, or other non-contact means. For use with emitters not projecting infra-red radiation, a laser range-finding sensor operating in the infrared range may be employed, such as a Keyence model LB-11/LB-70 displacement sensor/controller (Keyence corporation. Seattle, Wash.).

"Sonar ranging sensor" refers to a distance measuring device which by transmission and reception of ultrasonic pulses is capable of measuring the distance between two objects, stationary or moving.

Sonar-Controlled Apparatus for the Delivery of Electromagnetic Raditaion

In general, the present invention employs laser or sonar (a sensing method) to measure distance between a target and a source of EMR. The distance-registering non-contact sensor takes distance measurements at regular and small increments of time (eg. milliseconds or other adjustable increment) and automatically signals the EMR source control circuitry to vary either the position or the power output of the EMR source (as appropriate) in order to ensure that any change in distance is compensated rapidly and automatically. A remote, non-contact sensor takes measurements ("readings") of emitted radiation from the target during the period of EMR radiation, and these readings are recorded by an associated computer in a database. Further, should the emitted radiation sensor register a reading outside of preset limits, indicating that the target is no longer at the target site, the computer monitoring the readings notifies the EMR source control circuitry to switch off.

A preferred embodiment of the invention is a device, called a sonar-controlled heatbeam dolorimeter, for the measurement of pain tolerance. This preferred embodiment employs twin focused beam radiators directed at the skin target and a sonar range-finding device to constantly and accurately monitor the distance to the skin target. As this distance varies within limits due to natural involuntary movement of the operator holding the device, the power supply to the emitters is automatically altered by this invention so as to counter the effect of such movement on the energy delivered to the skin target, thus obviating the effect of such movement on stimulus temperature rate and maintaining this substantially constant at the desired incident intensity.

The sonar-controlled HBD device is employed in sensory testing of the subject. Sites to be tested and tolerance latencies measured thereat can be rendered more reproducible if first painted with a special matt-black paint formulated with iron oxide and with binders that do not form a palpable film on the skin, such that when dry the paint does not stimulate the mechanoceptive touch receptors of the skin. Typically the sites to be tested include the hands, arms, feet and chest of the subject, but can include other sites [see: Lipman, Blumenkopf and Parris, 'Chronic pain assessment using heatbeam dolorimetry' Pain 30:59–67 (1987)]. The subject to be tested is instructed in the sensory continuum of the pain sensibility range and instructed not to respond by movement until the 'pain tolerance limit' is reached. This is an unmistakable end-point with the HBD, a sudden and brisk sensation of unendurable pain resulting in movement of the instructed subject. The HBD is then directed to each body site in turn and the patient's movement at each test-site recorded automatically by the device's non-contact temperature measuring device, a thermopile, which records the cumulative thermal energy and exposure time required to reach the end-point at each site. The sites are tested multiple times, typically five (Lipman et al, 1987), as described above and the associated computer calculates various statistics characterizing the examination.

Figure 1A:
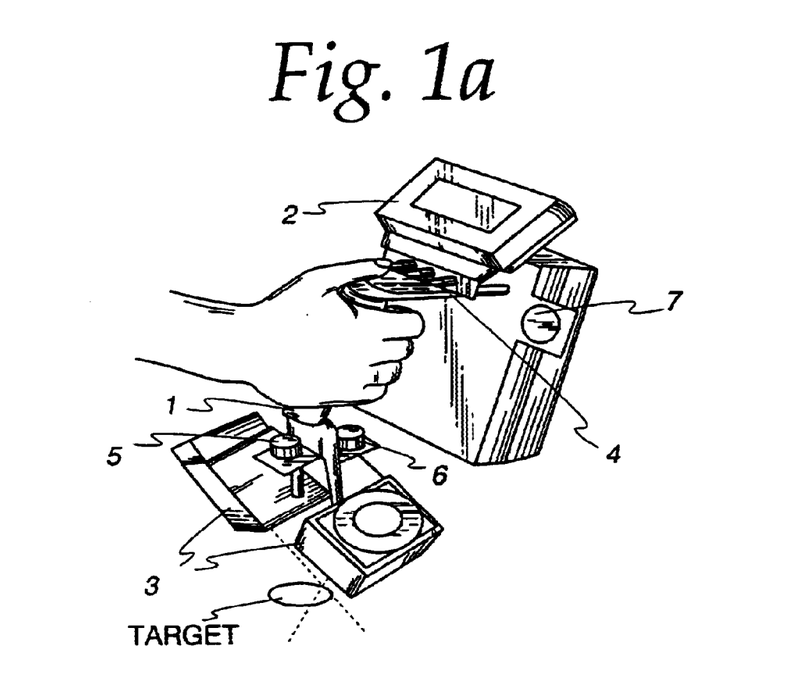
FIGS. 1a and 1b illustrates the hand-held component of the sonar-controlled dolorimeter, FIG. 1b showing detail of one of the two EMR emitters of the preferred embodiment.
Figure 1B:
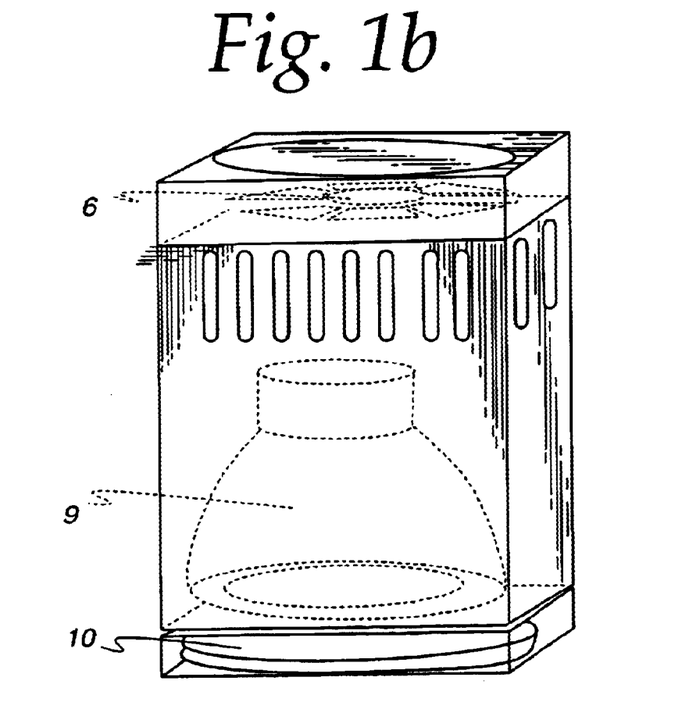
Figure 2:
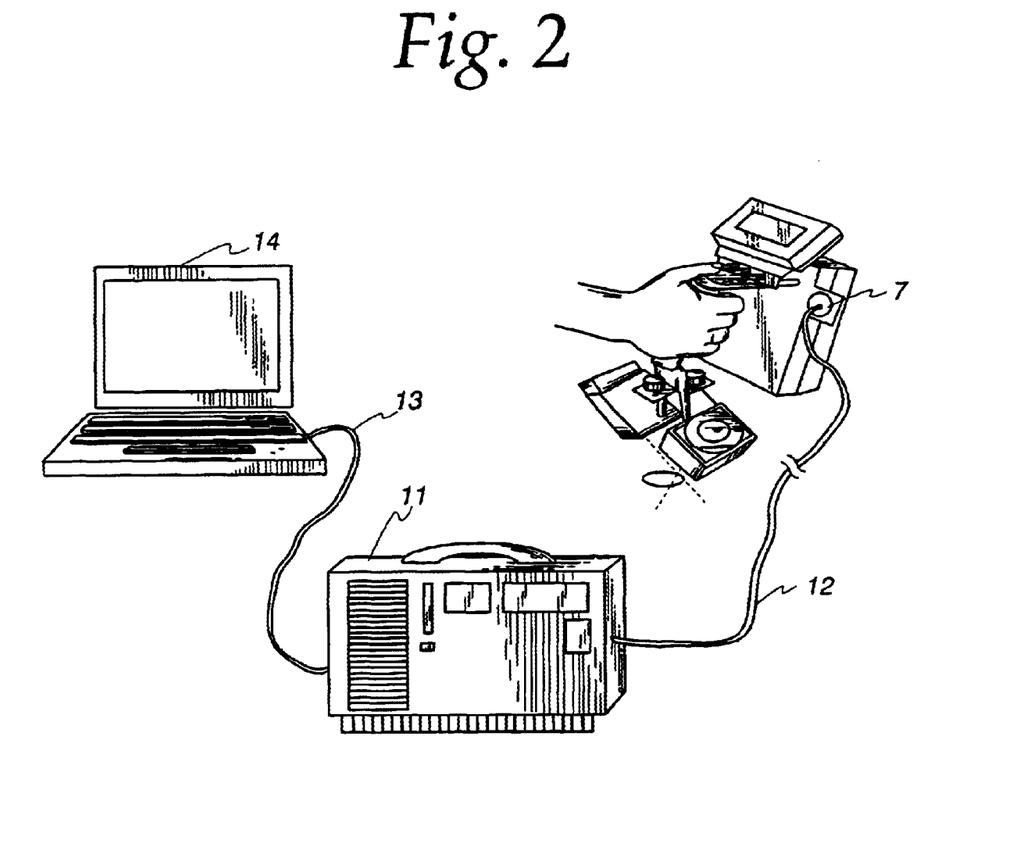
FIG. 2 illustrates the connection of the components of the device.

The Heatbeam Dolorimeter device employs a Pulse Width Modulated (PWM) variable power supply (20, in FIG. 3) capable of rapidly varying the intensity of the radiant heat of the emitters within certain limits, and with precision, under software control. Referring to FIGS. 1a and 1b and FIG. 2, the hand-held device (FIG. 1a), attached as shown in FIG. 2 to its power and control circuitry in the Control Unit 11 by a flexible umbilicus 12 which is connected to the hand-held portion of the device via a multipin amphenol connector 7 and operated by pressing the appropriate control buttons 4, employs as emitters two—and, optionally, more than two— infra-red projectors of heat and light (3 in FIG. 1a and, shown in detail in FIG. 1b), that are cooled by electrical fans 8 and geometrically arranged in the hand-held mechanical frame or support on which they are mounted 1 so that the region of overlapping intersection of their beams falls at the target site on the skin in an ellipse of the appropriate size and shape suitable for tolerance limit heatbeam dolorimetry. This target size is preferably of 2±0.3 inch major axis, and this is more preferably 1±0.1 inch, as adjusted and as appropriate. These emitters 3 may employ projector lamps 9, for example projector lamps manufactured by WICO (Niles, Ill.), type ENH. Other types of heat or light or other EMR projectors may be used, provided they meet requirements for energy delivery type, rate and effective control range. A sapphire lens 10 or other lens particularly offering low resistance to EMR transmission is mounted at the outlet of the two projectors. The hand-held device employs an electronic range-finding sensor 5, which can be either sonar or laser, the preferred embodiment using sonar, capable of measuring the distance to the skin target site with great precision (0.01 inch or better) and of refreshing this measurement at high frequency (settable, 0.1 Hz or faster). A non-limiting example of a suitable ultrasonic sonar sensor in the operating range of 4 to 40 inches and with a sample frequency of 0.1 Hz, is the M-5000 ultrasonic sensor with 0.25 mm (0.010 inch) precision, manufactured by Massa Instruments (Hingham, Mass.), employed in the preferred embodiment. As exemplified in FIG. 3, the sonar sensor 5 fulfils two functions: First, it provides feedback signals to the sonar controller 18, which can then signal the Liquid Crystal Display (LCD, 2) or any other suitable visual interface, to direct the operator in placing the HBD device at the approximately appropriate distance (at the midpoint of the effective control range as defined by look-up table FIG. 4) from the skin; and secondly, by means of the power control circuit 20 in the Control Unit 11 it provides feedback which controls the power output of the infra-red projectors 3. Thus, within the region of beam coincidence and within the region of sensor operation, which common envelopes are typically the effective control range, the hand-held HBD auto-regulates heat delivery in response to distance changes, to maintain the incident radiation delivered to the target at an 'ideal' and substantially constant rate, substantially equivalent, preferably statistically equivalent, to that which would be delivered had the device been stationary. In addition, the device employs a non-contact optical thermopile (thermocouple) sensor 6, such as an Exergen (Watertown, Mass.) Irt/c type, to measure infra-red emissivity of the skin at the target site, and the associated computer software records these measurements during the course of the assessment at a settable frequency, preferably of no less than 0.1 Hz.

Figure 3:
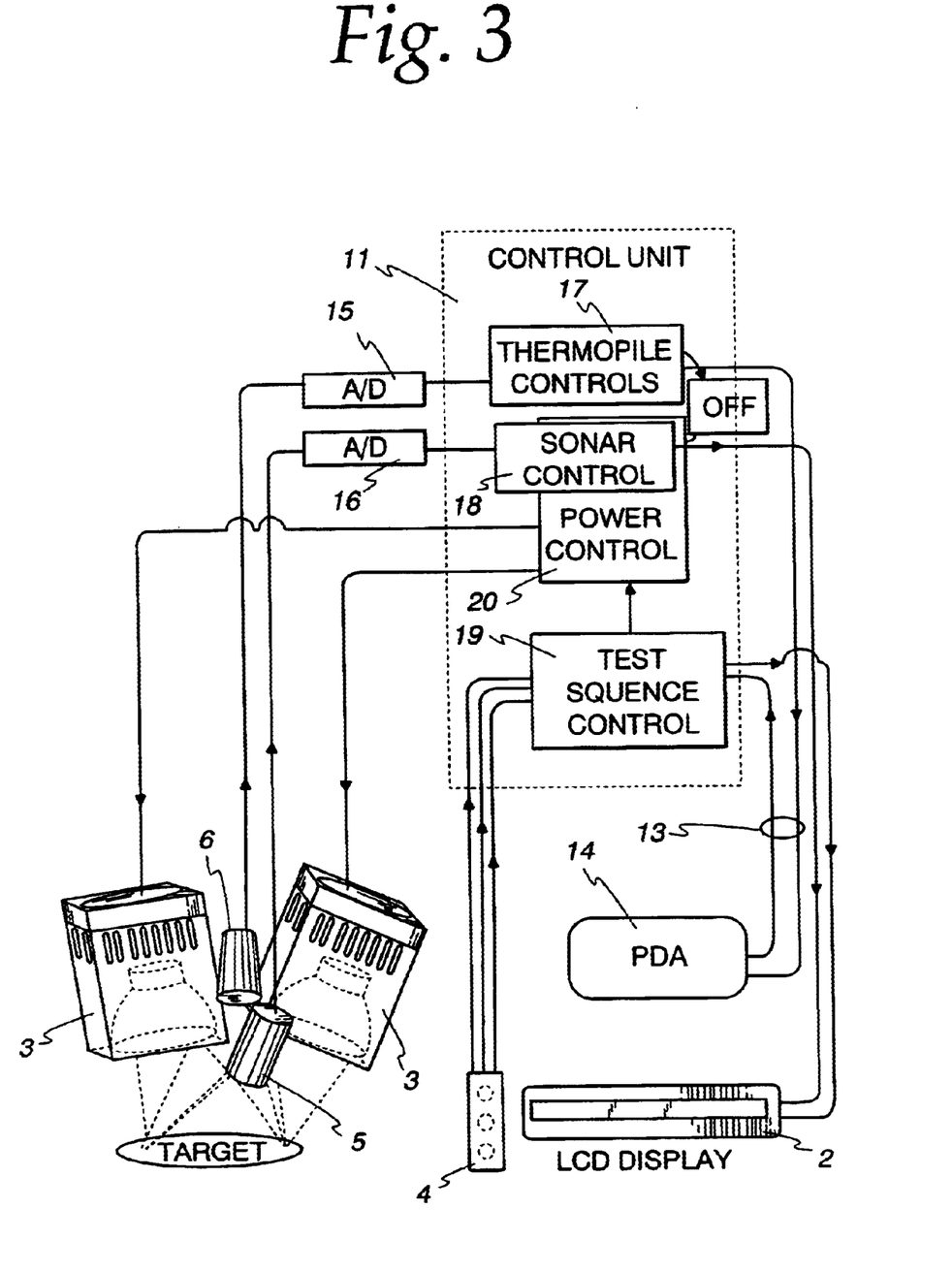
FIG. 3 illustrates the power and electronic information flow diagram of the device.

The connection of the components of the Sonar HBD are shown in FIG. 2 and FIG. 3. The power control unit 11, is connected at a connection site 7 to the handheld HBD unit by a flexible umbilicus 12, which in a preferred embodiment is Alpha (Sunbury-on-Thames, Middlesex, England) 9-pair 22 AWG foil shielded wire. In certain embodiments, power flows to the emitters through the umbilicus 12 as regulated by the power control 20. In certain embodiments, command signals to the Control Unit 11 are sent from the operator's push buttons 4 through the flexible umbilicus 12. In certain embodiments, distance data flow from the sonar ranging mechanism originating in the signal from the sonar sensor 5 are sent to the sonar control unit 18 through the flexible umbilicus 12. The operator initiates the test procedure and stores input data regarding the identity of the patient and related information at the hand-held computer interface 14 which may be, for example, a PDA (Personal Digital Assistant) or HPC (Handheld Personal Computer), or other interface, connected to the Control Unit 11 by a serial cable 13 through which sonar and thermopile data flow from the thermopile 17 and sonar 18 control circuits. The computer interface 14 may include commercially available database software for storing test data from the control unit 11 corresponding to the patient. The computer 14 can also include a conventional serial port for receiving data over the serial cable 13, as well as a standard operating system, such as Windows CE or Windows 98 from Microsoft, that provides application programming interfaces (APIs) that allow data from the serial port to be read by the database software.

Diagrammatically illustrated in FIG. 3 is the power and control information flow of the invention. Following data input to the hand-held computer 14 by the operator, and following sequence initiation by the operator pushing the appropriate button 4, the Test Sequence Logic Control 19 of the Control Unit 11 then directs the operator to test a particular part of the body, placing this instruction on the LCD display 2. After the operator acknowledges readiness by pushing the appropriate control button 4, sonar signals from the sonar sensor 5, having been digitized by the Analog to Digital Converter 16 are then used to control the LCD display output 2 and to guide the operator in manually positioning the device correctly. When correctly positioned according to the information displayed on the LCD, the operator pushes the appropriate button 4 to initiate the test stimulus, and the power control circuit 20, energizes the emitters 3 and automatically controls—increases or decreases, as appropriate—the power delivered to the emitters in response to sonar feedback 18 detected within the sonar circuits affiliated with the power control circuits 20. Both thermopile and sonar signals having been locally processed in the hand-held unit by the Analog to Digital converters (A/D) 15,16 and their digitized signals passed respectively to the thermopile control 17 and sonar control 18 circuits. When the subject's pain tolerance limit has been reached and they reflexively withdraw from the stimulus, the thermopile control circuits 17 detect this large change in site-emissivity monitored by the thermopile sensor 6 and signal the power controls 20 to stop emission. The Test Sequence Logic controller 19 then directs the operator to move to the next body site to be tested, displaying this information on the LCD display 2, and the test procedure continues and is repeated at the next site to be tested.

The functionality of the control unit 11 described above in connection with FIG. 3 can be implemented using one or more software programmable controllers (not shown), such as commercially available microprocessors, microcontrollers, or the like. In this implementation the controller can be coupled to a memory using a conventional bus. The memory can store one or more software programs for directing the control unit 11 to perform the functions, including the function of the thermopile controls 17, the sonar control 18, the power control 20, and the test sequence control 19, as described herein. The controller can also execute a software routine for interfacing the LCD 2 to the test sequence logic control 19 and the sonar signals.

Figure 4:
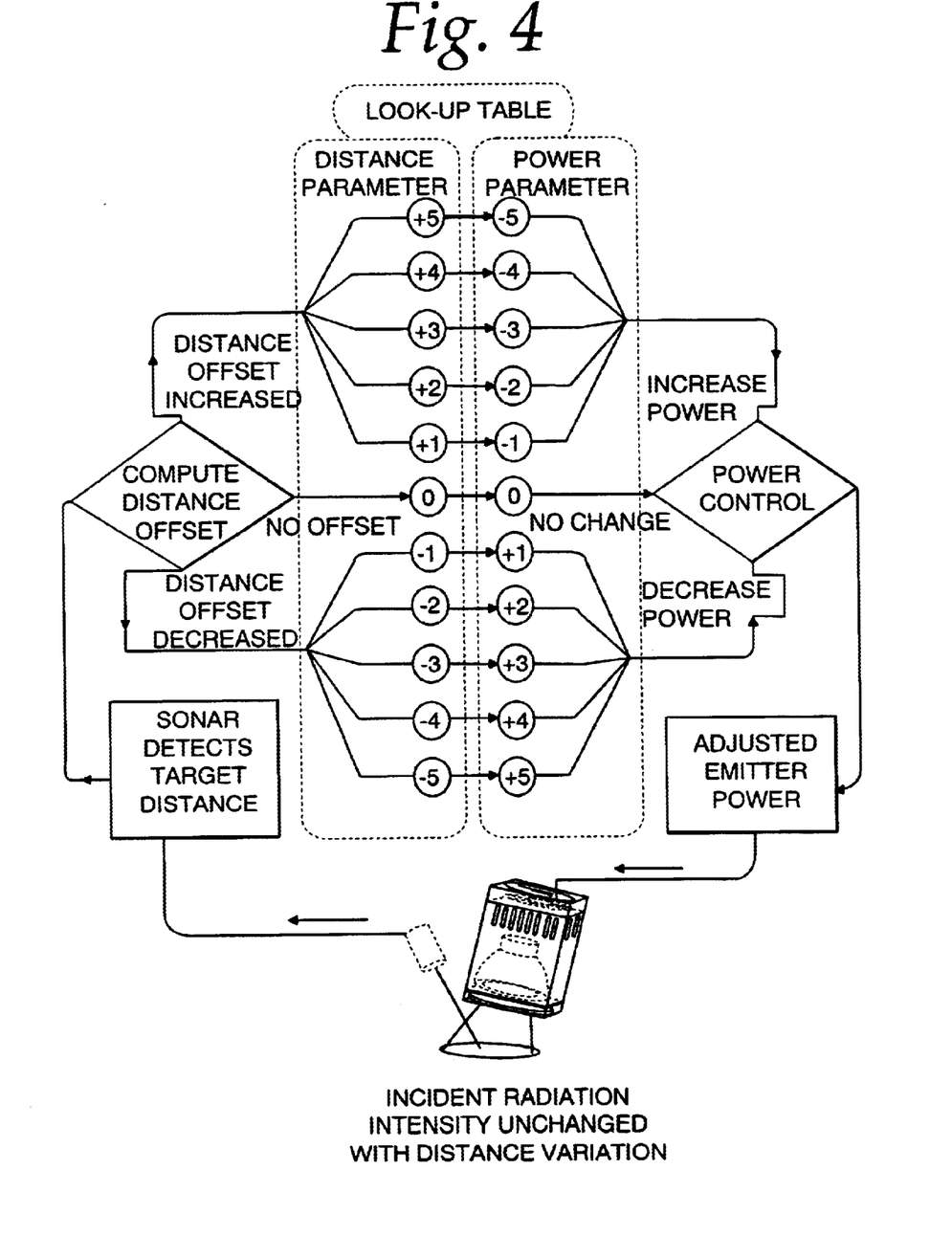
FIG. 4 illustrates the logic flowchart employed by the power control circuit in responding to the sonar control circuit, to maintain the radiation incident at the target at the desired constant intensity with changing distance.

The sonar control may include a software routine, executable by the controller, for regulating the power output of the emitters 3. The software may, for example, regulate the power output of the emitters 3 by utilizing a stored look-up table that contains pre-determined offset values. An example of logic of the sonar feedback procedure which may operate on the look-up table software procedure, is illustrated in FIG. 4. Represented in the figure is an example of a process whereby sonar signals are compared with software-stored norms representing the "nominal" or optimal operating distance. If this comparison indicates that the device is indeed held at the optimal (or 'nominal') distance, typically no change in emitter power occurs. If, however, an 'offset' is detected, either positive or negative, the software may route the offset signal to a location in the 'look-up' table corresponding to that specific offset distance (−5 to +5, in the distance parameter table of FIG. 4), triggering an instantaneous change in power offset compensation value (+5 to −5, in the power parameter table of FIG. 4), corresponding to the distance offset value. This power offset in turn modifies the power control (pulse width modulation) of the emitter and the energy transmitted therefrom. Thus, the closer that the sonar detects the target, the less power is applied to the emitter, and, conversely, the greater the distance detected by the sonar, the greater is the power applied to the emitter. Values of distance corresponding to the eleven steps from −5 to +5 may be empirically determined by an optical bench procedure (see below), and power offset values (−5 to +5) may be determined by a trial-and-error procedure during device calibration. Although the example and the figure describes for simplicity and for example, a sonar-controlled feedback procedure employing eleven distance/power stems, any number are possible depending on the effective control range and the characteristics of sensor type, power controls and emitter type. In another embodiment, the software may, for example, regulate the power output of the emitters 3 by means of a continuous solution of an equation for a distance, maintaining power at a desired level in response to varying distances.

SPECIFIC EXAMPLES

The following examples are provided by way of illustration and not limitation to enable one skilled in the art to appreciate the scope of the present invention and to practice the invention without undue experimentation. It will be appreciated that the choice of non-contact heat source, will be suggested to those skilled in the art in view of the disclosure herein in the examples that follow.

Example 1

Feedback Control Procedure

Demonstrated in the present example, a preferred embodiment provides a stable stimulus temperature at the target site and counters the effect of the tendency of a hand-held unit to move or change position under operator control upon the emission received by a target. The device achieves this automatic compensation for the effect of distance change by means of a look-up table procedure in the power control software. The process, illustrated in the flow diagram FIG. 4, was investigated using an optical bench apparatus.

Thus, regardless of tremor in the hand of the operator, the effect of the stimulus beam on target temperature is held substantially constant—at the value previously defined as producing the nominal temperature at the nominal distance of the arm-mounted version regardless of distance (within limits). Should the operator attempt to use the device outside of these limits the sonar will disengage the power to the beams, as a safety measure and to prevent fraud.

Demonstration of the Process:

Definition of the 'optimal' power at the 'optimal' or nominal distance was derived for the arm-mounted device, (called herein the "Basic HBD" or "Phase 0" model) using the optical bench apparatus. Under the experimental procedure followed, twenty seconds of thermal irradiation were applied to the a copper disc target by either the Basic HBD or by the present, improved, band-held sonar controlled HBD (called herein the Phase 2 or P2B HBD) at the optimal operating distance and the sensor temperature was noted at 0.4 sec intervals.

Static (Non-Moving) Testing:

Mounting the Basic (Phase 0) HBD device in the apparatus, the copper disc target was adjusted to the standard operating distance of the device and triplicate readings of temperature recorded over 20 seconds on the associated recording apparatus at 0.4 sec intervals. The Improved Sonar-regulated HBD (the "Phase 2B" HBD) was then mounted in place of the Phase 0 device and the sonar-regulating functionality was disabled. Next, with the sonar-controls of the Phase 2B device inoperative, so that feedback control would not be exerted, a range of different power values were manually input to the power control software of the hand-held Phase 2B HBD device at different distances from the sensor, such that by a trial-and-error method the appropriate power settings were obtained that generated at each distance the same target temperature as did the Basic (Phase 0) device at the single, optimal, distance at which that device is conventionally used. Power settings were obtained at 0.1 inch increments over a one-inch range centered on the 'optimal' distance for the focal geometry. The data are illustrated in FIG. 5.

Figure 5:
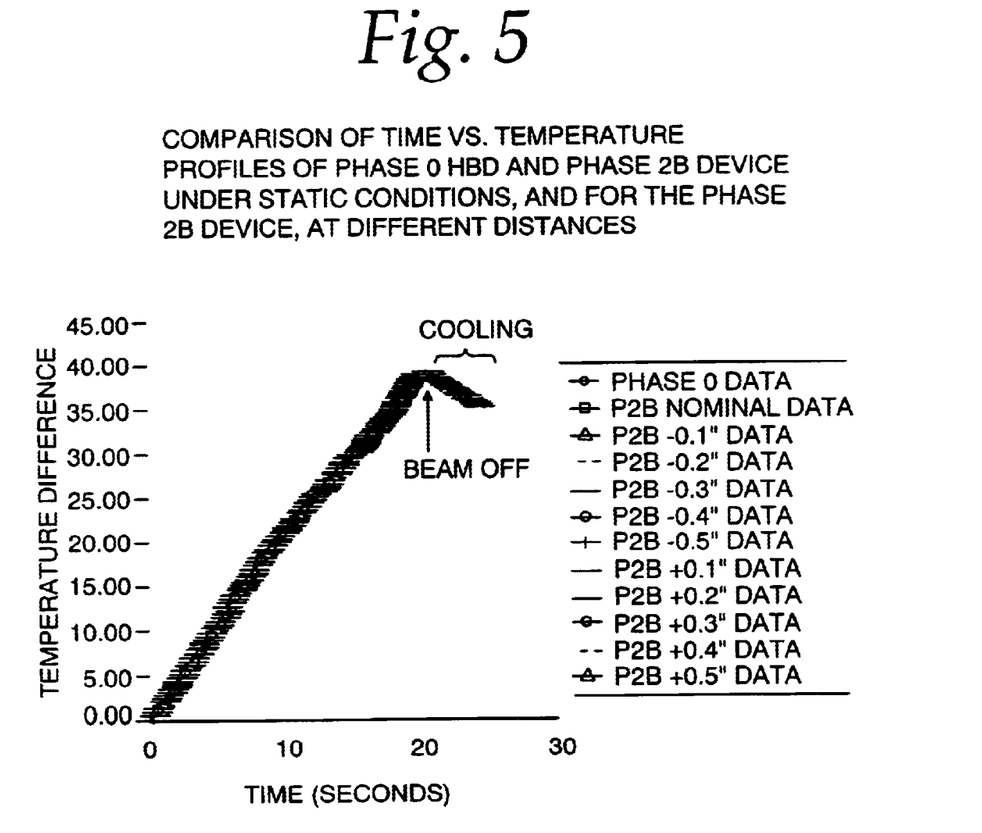
FIG. 5 illustrates the effect of incident radiation on a target emitted by the Basic HBD at a single distance, and compares this with the effect resulting from the present invention with sonar compensation disabled, at eleven different static (nonmoving) distances, each operated at a different 'beam power', to provide a calibration of the sonar-controlled device.

From FIG. 5 it can be seen that by means of the above optical bench method, power values ('Beam Values' of the Pulse Width Modulation power controls) were derived which enabled the improved sonar-controlled hand held Phase 2 HBD (called P2B in the figure), with sonar compensation functionality disabled, to achieve—at any one of eleven distances, in the present case—the same heating curve providing 1.93 Deg C/Sec. as had been previously achieved with the Basic HBD at the single optimal distance (Phase 0 HBD, in the figure). There was no statistical difference between Phase 0 temperature curves and any of the Phase 2B—generated curves at any distance ($p>0.05$).

Figure 6:
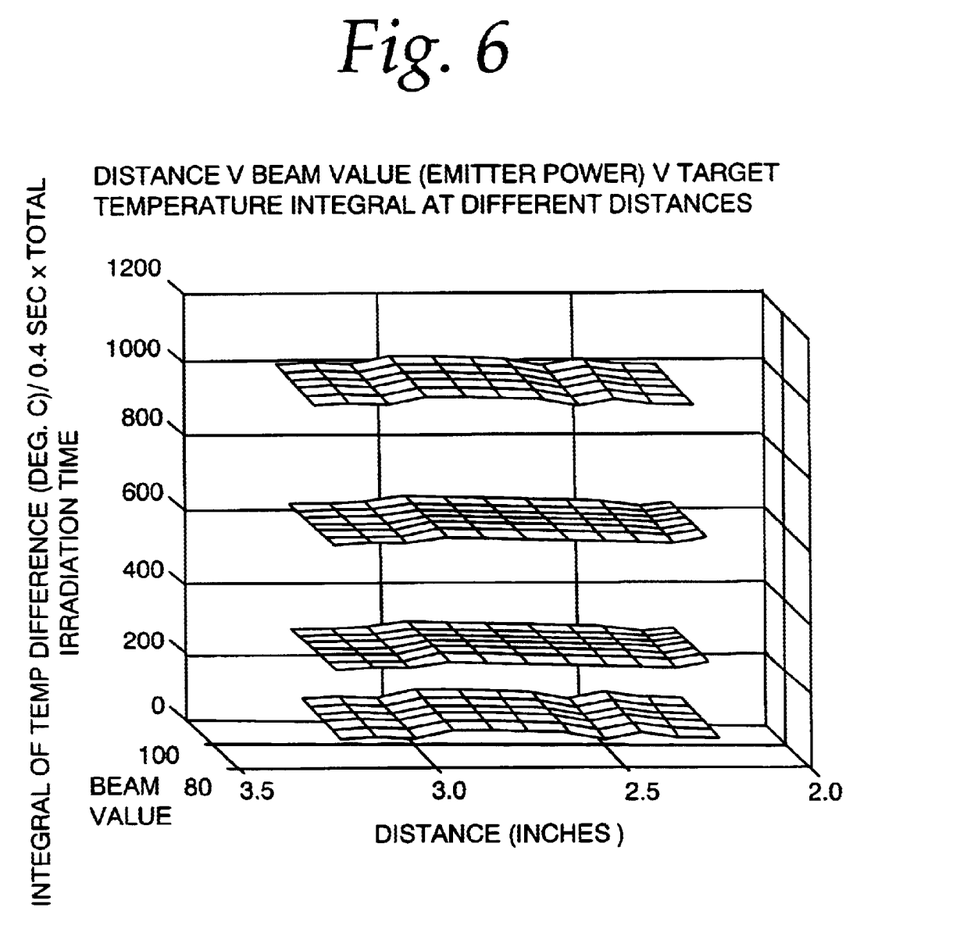
FIG. 6 illustrates the dependence of the cumulative target temperature (integral) upon both beam value (emitter power) and distance from the target under static (nonmoving) conditions.

Examining the precision and stability with which the emitter control circuitry and software of the Phase 2 device achieves stable temperature control by varying power ('beam value) with time fixed and at different distances, FIG. 6 illustrates the integrals of this relationship, which are as expected: the almost planar shape of the integral surfaces reveal good emitter control at each of the distances employed in this test and illustrate the dependence of target temperature on both power and distance.

Figure 7:
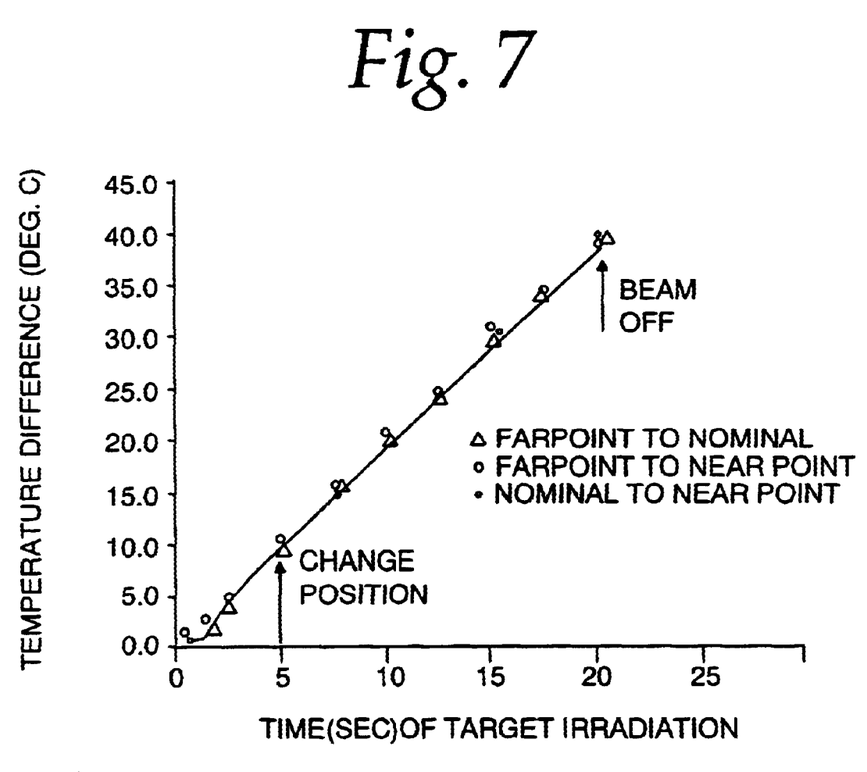
FIG. 7 illustrates the effect of incident radiation on a target produced by the present invention with sonar compensation functionality enabled and the device dynamically moved. Over a 20 Sec. irradiation of the target the device is moved to different distances and the effect remains the same as is was achieved with the nonmoving Basic HBD.

Dynamic Testing:

The above-derived power values from the optical bench study illustrated in FIG. 5 were then input as parameters into the power control feedback software, so that the device would autoregulate power output in response to detected changes in sonar-ranging distance to the target sensor according to the algorithm of FIG. 4. The optical bench procedure was then employed to dynamically vary the HBD-target distance, in order to detect and measure such dynamic autoregulation: the HBD being driven either away from or toward the target during the 20 second heating period. FIG. 7 illustrates these data with the improved Sonar (Phase 2B) HBD being moved toward the target (at the fifth second, arrow in FIG. 7) from the far point to the 'nominal' operating distance, then from the far point to the near point, and from the nominal distance to the near point. All three curves (which are the means of replicates) are essentially coincident ($R^2=0.98$, $p>0.05$). Thus, the sonar controlled feedback regulation of beam power with distance successfully auto-regulates a substantially constant heating profile at the target, and, further, regardless of distance and regardless of movement, the improved hand-held Sonar HBD achieves the same heating characteristics as the Basic (arm-mounted) HBD device within the limits tested.

The invention now being fully described, it will be apparent to one of ordinary skill in the art that many changes and modifications can be made thereto without departing from the spirit or scope of the invention as set forth therein. The examples described herein illustrate the methods and devices of the invention. These examples are intended to be merely illustrative of the present invention, and not limiting thereof in either scope or spirit. Those skilled in the art will readily understand that variations of the components, methods, steps, and devices described in these examples can be used. All references cited herein are incorporated by reference in their entirety.

What is claimed is:

1. A non-contact apparatus for regulating delivery of electro-magnetic radiation (EMR) to a target site, said apparatus comprising:

a non-contact emitter;

a distance sensor; and an emitter control device, wherein said delivery of electromagnetic radiation is automatically regulated as a function of target-site distance through interaction of the distance sensor and the emitter control device; wherein the non-contact emitter is a radiant heat source; wherein the distance sensor is a sonar-ranging sensor; wherein the emitter control device is a radiant heat source control device; wherein said apparatus provides an automatically-controlled heating rate at the target site when the target-site distance changes but remains within an effective distance range; wherein the target site is a site on a subject's skin; and wherein the apparatus is a dolorimeter for determining pain tolerance, said apparatus further comprising a non-contact temperature-measuring device, wherein said apparatus is capable of being employed for determining pain tolerance without tactile stimulation of the site on the subject's skin by said apparatus or by any other means.

2. The apparatus of claim 1 wherein said automatic regulation provides a controlled effect at the target site when the target-site distance changes within an effective control range.

3. The apparatus of claim 1 further comprising a hand-held fixture, wherein the dolorimeter is capable of being held by a dolorimeter operator.

4. A method for regulating delivery of electromagnetic radiation to a target site comprising the steps of:

(a) delivering electro-magnetic radiation;

(b) determining a target-site distance during the step of delivering electro-magnetic radiation; and (c) automatically regulating the delivery of electro-magnetic radiation as a function of the target-site distance;

wherein the step of delivering electro-magnetic radiation comprises delivering radiant heat; wherein the step of determining the target-site distance utilizes sonar; wherein the target site is a site on a subject's skin;

said method further comprising (1) determining temperature of the target site without contacting the target site and (2) providing the apparatus of claim 1 for carrying out the steps of delivering radiant heat, determining the target-site distance, automatically regulating the projection of radiant heat, and determining the temperature of the target site;

wherein said method is capable of determining pain tolerance without tactile stimulation of the site on the subject's skin.

5. The method of claim 4 wherein said step of automatically regulating provides a controlled effect at the target site when the target-site distance changes within an effective control range.

* * * * *